United States Patent [19]

Ryu et al.

[11] 4,415,745

[45] Nov. 15, 1983

[54] PROCESS FOR THE PREPARATION OF AROMATIC CARBAMATES AND ISOCYANATES

[75] Inventors: Ji-Yong Ryu, Ramsey; Arthur M. Brownstein, Wycoff, both of N.J.

[73] Assignee: Exxon Research & Engineering Co., Florham Park, N.J.

[21] Appl. No.: 343,583

[22] Filed: Jan. 28, 1982

Related U.S. Application Data

[63] Continuation-in-part of Ser. No. 290,005, Aug. 4, 1981, which is a continuation of Ser. No. 179,062, Aug. 18, 1980, abandoned.

[51] Int. Cl.$^3$ .................. C07C 125/06; C07C 118/00
[52] U.S. Cl. .................. 560/25; 260/453 P
[58] Field of Search .................. 260/453 P; 560/25

[56] References Cited

U.S. PATENT DOCUMENTS

| | | | |
|---|---|---|---|
| 2,860,166 | 11/1956 | Newcamer et al. | 560/24 |
| 3,029,245 | 4/1962 | Aries | 260/294.9 |
| 3,462,476 | 8/1969 | O'Donnell et al. | 260/465 C |
| 4,202,986 | 5/1980 | Shawl | 560/25 |

OTHER PUBLICATIONS

Altankirk et al., J. Org. Chem. 27, 4532 (1962).

*Primary Examiner*—Dolph H. Torrence
*Attorney, Agent, or Firm*—Robert A. Maggio

[57] ABSTRACT

Production of aromatic polyisocyanates is achieved by a multireaction process comprising sequentially; the ammoxidation of a methylated aromatic, e.g. toluene; hydrolysis of the aromatic nitrile; conversion of the resultant amide to a carbamate; condensation with aldehyde; decomposition of the condensation product; and, recovery of the aromatic polyisocyanate.

8 Claims, No Drawings

PROCESS FOR THE PREPARATION OF AROMATIC CARBAMATES AND ISOCYANATES

CROSS REFERENCE TO RELATED APPLICATIONS

The present application is a continuation-in-part of U.S. patent application Ser. No. 290,005, filed Aug. 4, 1981, which is a continuation of U.S. patent application Ser. No. 179,062, filed Aug. 18, 1980, abandoned, the disclosures of which are herein incorporated by reference.

BACKGROUND OF THE INVENTION

This invention relates to the production of aromatic polycarbamates and polyisocyanates. More particularly, it relates to the preparation of aromatic polycarbamates and polyisocyanates from alkylated aromatic compounds such as toluene via a multireaction step process.

Polyurethanes fill a very important commercial need in both the flexible and rigid plastic fields. For both the flexible and rigid types, the urethane is the product of the reaction of an alcohol and an isocyanate. Much effort and time is being spent on developing a means for producing these isocyanates in a less expensive and/or less toxic manner. Desirable isocyanates for flexible and rigid plastic applications include methylene bis-(phenyl isocyanate) (hereafter designated as MDI) and polymeric polyisocyanates such as polymethylene polyphenyl isocyanates (hereafter designated as PMPPI).

There are two conventional processes for the manufacture of isocyanates such as MDI or PMPPI, namely, phosgene technology and carbonylation technology.

(1) Phosgene technology which may be illustrated as follows:

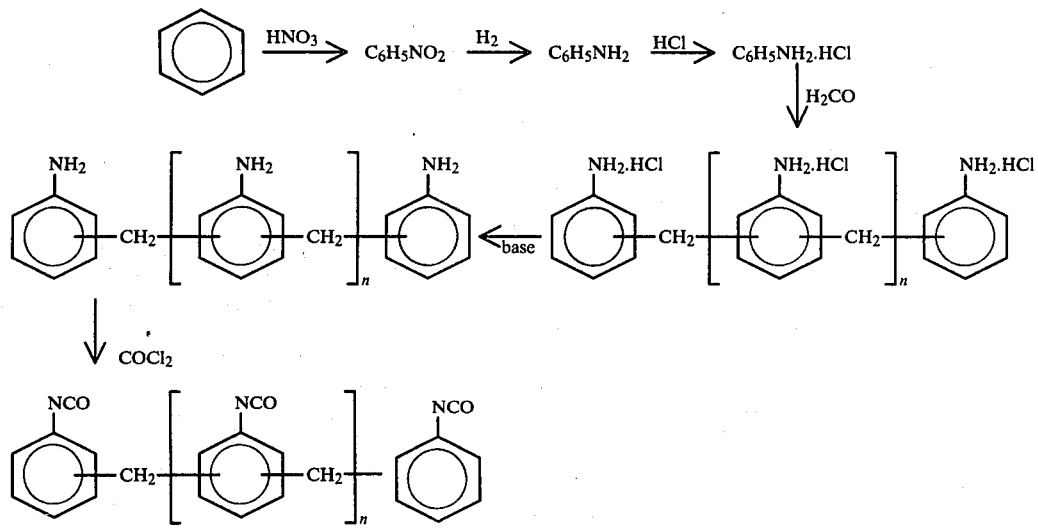

wherein n is zero or an integer ranging from 1 to 5 for the product is generally a mixture of various molecular weight oligomers.

Thus, for the desired isocyanate compounds n is zero for MDI and n is 1 to 5 for PMPPI. The reaction product providing the latter usually includes some MDI.

A variation of the phosgene technology employs the ammoxidation of xylene to the corresponding dinitrile, i.e. terephthalonitrile $C_6H_4(CN)_2$. However, the resulting dinitrile is converted to xylene diamine $[C_6H_4(CH_2NH_2)_2[$ which in turn is converted to 1,4-xylylene diisocyanate via phosgenation. This overall process is different from the present invention.

The phosgene approach is highly unsuitable since the reactant phosgene gas is highly toxic and the process highly wasteful of material and energy since a reactant $HNO_3$ is manufactured by oxidation of ammonia ($NH_3$) and after nitration of benzene to nitrobenzene it is reduced. One approach to overcoming the wastefulness of the process was to directly aminate the benzene with ammonia as is taught in U.S. Pat. No. 4,031,106. However, this approach is not yet commercially useful because of the inefficiency of the amination, even under severe reaction conditions.

(2) Carbonylation technology

In order to overcome some of the deficiencies of the phosgene technology, a carbonylation approach has been developed which may be expressed as follows:

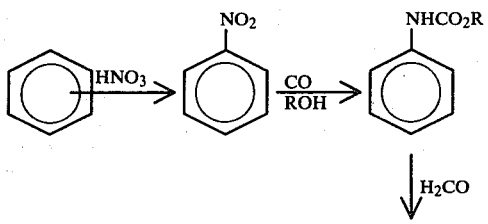

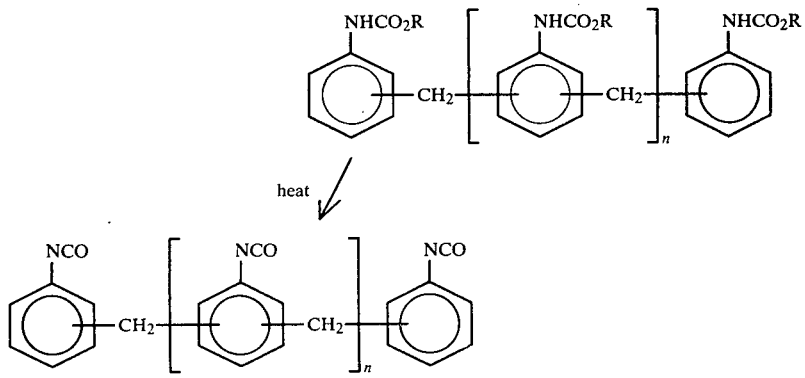

wherein n is as earlier defined and R represents a hydrocarbyl radical, usually a $C_1$ to $C_5$ lower alkyl such as methyl. (See for example: Chemical Week, Nov. 9, 1977, pp 57-58).

This carbonylation technology overcomes some of the defects of phosgene technology by eliminating use of the toxic phosgene gas, HCl and NaOH. However, there are defects in carbonylation technology which include:

(1) use of more expensive CO in place of hydrogen;
(2) high pressure equipment is required for carbonylation of nitrobenzene to carbamate;
(3) use of expensive metal compounds or toxic material, e.g. selenium as a catalyst; and,
(4) recycle of unconverted CO to the high pressure reactor requires energy.

Because of these defects which are apparent in the teachings of U.S. Pat. No. 4,038,377 and German DOS No. 2,635,490, the carbonylation technology has little advantage over the phosgene technology.

It is an object of this invention to overcome many of the defects of the process technology currently used to produce MDI and PMPPI.

SUMMARY OF THE INVENTION

It has been discovered that the disadvantages of the prior art processes can be overcome by producing, in one embodiment, aromatic polycarbamates, and optionally and preferably from these carbamates polyisocyanates such as MDI and PMPPI, by a multi-step process comprising sequentially; the ammoxidation of alkylated aromatic compounds, e.g., toluene, to form nitrile containing compounds; hydrolysis of the aromatic nitrile group to an amide group; conversion of the resultant amide to a carbamate; condensation of the carbamate with a carbonyl containing compound; decomposition of the condensation product; and, recovery of the aromatic polyisocyanate.

This multi-step process can be expressed as follows when using toluene as the alkylated aromatic compound.

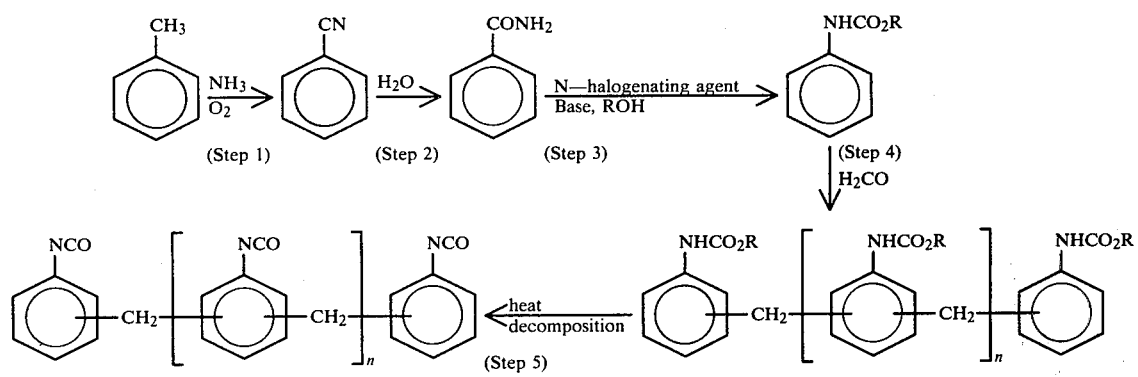

wherein n is as earlier defined and R represents a lower alkyl group containing from 1 to 10 carbons.

This novel multireaction step process provides the improvements of: abundant, less expensive and less toxic primary reactants, e.g., toluene and ammonia; a saving of energy and material, and elimination of the corrosive nitric acid for the production of nitrobenzene by use of ammonia; elimination of extremely toxic compounds such as the reactant phosgene and catalyst selenium compounds; a by-product (NaCl) can be recycled to produce halogen and base for energy savings and reduction of pollution costs; no high pressure equipment is required to carry out any reaction step; and, a carbamate synthesis step which has high selectivity and high amide conversion.

DETAILED DESCRIPTION OF THE INVENTION

The raw material sources for the aromatic polyisocyanate are alkylated, preferably methylated, aromatic compounds (preferably toluene), ammonia and water.

The new aromatic isocyanate process consists of four steps as earlier stated to produce the aromatic polycarbamates, and an optional fifth step to produce the polyisocyanates therefrom which are:

1. ammoxidation of alkylated aromatics (preferably toluene) to form a nitrile containing compound;

2. hydrolysis of aromatic nitrile (preferably benzonitrile) to form an amide;
3. conversion of the amide to a carbamate;
4. condensation of the carbamate with a carbonyl containing compound; and, optionally
5. conversion of poly(carbamate) to polyisocyanate.

To the best of our knowledge, no prior art or current commercial processes teach that aromatic isocyanates can be synthesized economically with high yield by arranging a number of reaction steps in the specific sequential way as in this invention.

The above described steps of the process of the present invention are hereinafter discussed in detail.

(1) Ammoxidation of Alkylated Aromatics

The vapor phase ammoxidation useful herein is shown generally in U.S. Pat. Nos. 3,462,476 and 3,801,619 (the disclosures of which are incorporated herein by reference) as a catalytic transformation of an alkylated aromatic compound in the presence of ammonia, air and water into the corresponding aromatic nitriles.

Thus, it is contemplated that the aromatic compound which undergoes ammoxidation can be represented by the structural formula:

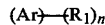  (I)

wherein Ar can be a halogen substituted or unsubstituted aromatic hydrocarbyl group, typically an aromatic hydrocarbyl group, having from 6 to 14, preferably from 6 to 10, and most preferably 6 carbons; $R_1$ is alkyl (straight or branched chain) having from about 1 to about 10, preferably from about 1 to about 5, and most preferably from about 1 to about 3 (e.g., 1) carbons; and n is a number of from about 1 to about 5 (e.g., to 1 to 4 if polymeric end products are desired) preferably from about 1 to about 3, most preferably from about 1 to about 2 (e.g., 1). Thus, while it is most preferable to employ methylated aromatic compounds based on economic considerations, it is possible to employ higher carbon number alkyl substituent groupings on the aromatic ring, since they will eventually result in the formation of cyano substituted aromatic compounds. Halogen substituents can be present on the Ar hydrocarbyl group to impart fire retardancy to the ultimate end product into which the resulting aromatic isocyanate can be incorporated.

Representative examples of suitable alkylated aromatic compounds which can be employed in the ammoxidation step include, toluene, p-xylene, m-xylene, o-xylene, mesitylene, ethylbenzene, p-cymene, cumene, chlorotoluene, alphamethyl naphthalene, and mixtures thereof. It is to be understood that not all alkyl groups on the aromatic compound need to be converted to cyano groups, only that at least one alkyl group be so converted. Thus, the resulting nitrile can be represented by the structural formula:

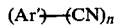  (I$_a$)

wherein Ar' is as described in connection with structural formula II below, and n is as described in connection with structural formula I.

For the purposes of this invention it is preferred that when toluene is employed as a reactant, it be converted in high yield, i.e. greater than 90 mole %, to benzonitrile. Consequently, the use of a catalyst providing such yields, e.g. vanadia-chromia on an alumina support, is also preferred. If desired, ammoxidation of alkylated aromatic compounds can be carried out in two steps, instead of one step, as is taught in U.S. Pat. No. 3,029,245, the disclosure of which is herein incorporated by reference.

As taught in British Patent Specification No. 946,916, the disclosure of which is herein incorporated by reference, while aromatic nitriles such as benzonitrile can be synthesized via liquid phase ammoxidation of methylated benzenes, the selectivity to benzonitrile is not as high as the vapor phase ammoxidation of toluene, amides also being produced as a by-product. However since benzonitrile will be hydrolyzed to benzamide in the process of the present invention, the small amount of benzamide produced during the liquid phase ammoxidation is a useful by-product and hence improves the overall yield. Consequently, liquid phase ammoxidation can also be employed in the present invention.

(2) Hydrolysis of Aromatic Nitriles

In this step, any of the aromatic nitriles from the first step have at least one of the cyano groups present thereon converted to the corresponding amide group by generally known methods. The resulting amide can be represented by the structural formula:

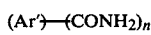  (II)

wherein n is as described in connection with structural formula I; Ar' can be a substituted or unsubstituted aromatic hydrocarbyl group said hydrocarbyl group (exclusive of substituents) being as described in connection with Ar of structural formula I, said substituents being selected from halogen (i.e., F, Cl, Br, I), alkyl, said alkyl being as defined in connection with $R_1$ of structural formula I, and mixtures thereof, the number of said substituents typically not being greater than 5−n, preferably not greater than 4−n, and most preferably not greater than 3−n. Methods for conducting this procedure are described in British Patent Specification Nos. 1,133,013; and 1,351,530; as well as M. J. Coor et al, Chem. Comm. 5 121 (1966); Ger. DOS No. 2,131,813 and U.S. Pat. No. 3,656,307, the disclosures of which are herein incorporated by reference. For example, one synthetic method employs a procedure wherein an aqueous solution or emulsion of a nitrile is passed (e.g., at 70° to 100° C. and atmospheric pressure) at a controlled rate through a bed of manganese dioxide with the nitrile being converted to an amide that is recovered in the effluent. Metal hydroxide catalysts can also be employed in the amide synthesis.

(3) Conversion of Amide to Carbamate

In this step at least one of the amide groups resulting from step 2 is converted to its corresponding carbamate group by any method capable of achieving this effect.

The amide reactant of this step of the invention is described in structural formula II. In order to eventually permit the formation of polymeric aromatic carbamates through the condensation reaction described hereinafter, there should be at least two available hydrogens on two of the aromatic carbons of the aromatic amide. Representative amides include benzamide (preferred), toluamide, toluenediamide and phthalamide. More specifically, in accordance with conventional procedures the conversion of amide to carbamate can be considered to result from three sequentially separate reactions:

1. $(Ar')\text{-}(CONH_2)_n + \text{N-halogenating agents} \rightarrow (Ar')\text{-}(CONHX)_n$. N-halogenating agents are those known generally in the art and include halogens such as chlorine and bromine, alkyl, and aryl hypohalites, such as t-butyl hypochlorite, t-butyl hypobromite, acetyl hypochlorite and acetyl hypobromite and compounds of the formula MOX wherein M is a Group IA or Group IIA metal of the Periodic Table and X is halogen (B. Altankirk et. al. synthesized N-chlorobenzamide by using t-butyl hypochlorite with 71% yield (J. Org. Chem., 27, 4532 (1962));

2. $(Ar')\text{-}(CONHCl)_n + \text{Base} \rightarrow (Ar')\text{-}(NCO)_n + \text{salt}$ (known as the Hoffmann rearrangement); and 3. $(Ar')\text{-}(NCO)_n + ROH \rightarrow (Ar')\text{-}(NHCO_2R)_n$ wherein Ar', and n are as defined in connection with structural formula II.

Current practices teach that these reactions must be carried out under anhydrous conditions to achieve high carbamate yield. If these reactions are carried out in the presence of water, a number of undesirable side reactions can occur. For example, if N-chlorination of benzamide is carried out in the presence of water, part of the N-chlorobenzamide formed in decomposed to benzamide. In addition, other undesirable side reactions occur such as:

$$C_6H_5NCO + H_2O \rightarrow C_6H_5NH_2 + CO_2; \text{ and}$$
$$C_6H_5NH_2 + C_6H_5NCO \rightarrow C_6H_5NHCONHC_6H_5$$

In fact, the Hoffmann hypobromite reaction is used for the preparation of amines, e.g., $R\text{—}CONH_2 + Br_2 + 4NaOH \rightarrow R\text{—}NH_2 + Na_2CO_3 + 2NaBr + 2H_2O$.

According to the teachings of the art in order to produce isocyanates, the reactions have to be carried out under anhydrous conditions and, hence, Group IA alkoxides, such as sodium methoxide, have been used as the base of the Hoffmann rearrangement. Low temperatures, preferably less than 5° C. are also desirable for high yields.

Application of the Hoffmann rearrangement for the manufacture of isocyanates and arylalkylamines can be found in Japanese Pat. No. 54-128521 and French Pat. No. 1,007,001, the disclosures of which are herein incorporated by reference, e.g., n-propyl isocyanate is obtained in 86.7% yield at 97.4% conversion of N-chlorobutylamide by using bicyclic amidine as base.

Another difficultly with conventional procedures is that the produced benzamide can react with phenyl isocyanate to form an insoluble precipitate, when the reaction temperatures are below about 40° C., e.g., $C_6H_5CONH_2 + C_6H_5NCO \rightarrow C_6H_5CONHCONHC_6H_5$.

While the aforedescribed sequential procedure with its attendant side reactions can be employed in this step it is not preferred. A much more preferred and commercially desirable approach for conversion of the amide to carbamate can be achieved in high yield in the presence of water by carrying out the three reactions simultaneously, instead of carrying out three reactions in sequence.

The preferred technique for carrying out the three reactions simultaneously involves simultaneously reacting an aryl amide and an N-halogenating agent in the presence of alcohol at a temperature of from about 40° to about 200° C., while maintaining the pH of the resulting reaction medium of from neutral to basic by the addition of an aqueous solution of base, e.g., said base being selected from the group consisting of NaOH, KOH, LiOH, and tri-alkyl amines, and while continually mixing the reactants for a period of from about 1 minute to 10 hours, and thereafter recovering the carbamate product.

Thus, simultaneous addition of N-halogenating agents and base solution to an amide solution is preferred. If desired, the base solution, or part of the base solution, can be premixed with the amide solution prior to entering into the reactor. The preferred reaction temperature is approximately higher than 40° C. when methanol is used to convert the phenyl isocyanate to carbamate. For example, somewhat higher temperature is preferred for ethanol than for methanol. The preferred solvents for the amide solution and the reaction medium are alcohol (e.g. ethanol, methanol and mixtures) and mixtures of alcohol with other organic solvents. The aqueous base solution typically is diluted with organic solvents such as an alcohol. Preferred bases are sodium, potassium and lithium hydroxides and trialkyl amines. If the aqueous base solutions are very dilute i.e. less than about 10 weight percent, addition of MX salts, e.g., NaCl, to base solutions or saturation of base solution, with salts is preferred to reduce side reactions in which water is involved directly or indirectly to improve amide conversion and product yields. The preferred base solution contains from 5 to 90, more usefully from 30 to 80, and at least 2, weight percent water. The preferred N-halogenating agents are hypohalites such as t-butyl hypochlorite, sodium hypochlorite, sodium hypobromite, sodium hypoiodite, chlorine, bromine, iodine, $Cl_2O$, $I_2O$ and $Br_2O$. If desired, the N-halogenating agents can be diluted with solvents, such as alcohol, t-butanol or $CCl_4$, or inert gases for use in a large commercial reactor to improve yield and for safety. Since N-halogenating agents are very reactive under reaction conditions, multiple injection can be employed for large reactor operations. The preferred pH range of the reaction medium is from neutral to basic. Here, neutral means approximately 6 to 8 pH. Rapid mixing of the reactants in the reactor is preferred to reduce undesirable side reactions.

A more detailed description of this preferred step is provided in copending application Ser. No. 179,065 filed Aug. 18, 1980 and of common assignee, the disclosure of which is incorporated herein by reference. Alternatively, the carbamates may be synthesized from the aforedescribed amides in accordance with the procedures disclosed in U.S. Pat. No. 2,860,166 the disclosure of which is herein incorporated by reference.

The resulting carbamates can be represented by the structural formula:

$(Ar')\text{-}(NHCO_2R_2)_n$     (III)

wherein $R_2$ can be independently selected from alkyl, typically alkyl having from about 1 to about 10, preferably from about 1 to about 5, and most preferably from about 1 to about 3 (e.g. 1 to 2) carbons, aryl, typically aryl having from about 6 to about 14, preferably from about 6 to about 10, and most preferably 6 carbons, alkaryl and aralkyl wherein the aryl and alkyl groups thereof are as described above, and cycloalkyl, typically cycloalkyl having from about 4 to about 10, preferably from about 6 to about 10, and most preferably from about 6 to 8 carbons.

(4) Condensation of Carbamate With Carbonyl Compound

The aforedescribed carbamates are condensed with carbonyl containing compounds such as aldehydes or ketones in accordance with conventional methods such as described in U.S. Pat. Nos. 2,946,768; 4,146,727; 4,162,362; 4,172,948; and 4,202,986 the disclosures of which are herein incorporated by reference. Representative carbonyl compounds include formaldehyde, paraformaldehyde, or any other aldehyde or ketone, which preferably is not too bulky to permit the condensation reaction, the most commercial carbonyl compound being formaldehyde. The quantity of carbonyl compound employed relative to the carbamate is controlled to achieve the degree of condensation or polymerization desired in the reaction product. Generally the molar ratio of carbamate to carbonyl compound, e.g., formaldehyde, will vary typically from about 1.5:1 to 8:1. At the high end of this range, production of dimeric carbamates will predominate, whereas at the low end of the range, the higher polyalkylene polyarylene carbamates will predominate; the particular ratio of oligomers being controlled in accordance with the particular properties sought to be imparted to the polyurethane into which the final isocyanate will be incorporated. Condensation reaction temperatures can vary widely and typically will vary from about 25° to about 170° C., e.g., 50° to 130° C. Catalysts, solvents, and other reaction parameters are disclosed in the aforedescribed patents and are conventional. A preferred procedure is disclosed in U.S. patent application Ser. No. 179,063 filed Aug. 15, 1980; now abandoned, the disclosure of which is herein incorporated by reference. This application discloses the use of a heterogeneous catalyst in the form of a solid, sulfonic acid material typically employed as a sulfonic acid substituted ion-exchange resin. Reaction temperatures typically vary from about 25° to 200° C., preferably 50° to 150° C. For example, the solid, sulfonic acid, heterogeneous catalyst material may be such conventional acid ion-exchange resins as DOWCX50WX8 TM, Amberlyst 15 TM, Duolite C-20 TM, which typically have a polystyrene backbone with sulfonic acid substituents on the aromatic rings, or a perfluoroalkylene backbone with pendant sulfonic acid groups.

The resulting carbamates can be represented by the structural formula:

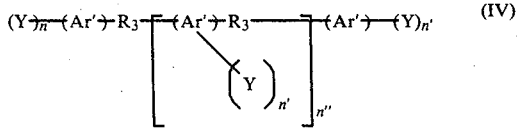

(IV)

wherein: Y represents the group —NHCOOR$_2$, R$_2$ being as described in connection with structural formula III; R$_3$ can independently be alkylene, typically alkylene having from about 1 to about 10, preferably from about 1 to about 5, most preferably from about 1 to about 3 (e.g. 1) carbons, arylene, typically arylene having from about 6 to about 14, preferably from about 6 to about 10, and most preferably 6 carbons, aralkylene and alkarylene wherein the alkyl and aryl groups thereof are as described immediately above, and cycloalkylene, typically cycloalkylene having from about 4 to about 10, preferably 6 to about 10, and most preferably 6 to about 8 carbons; Ar' is as described in connection with structural formula III; n' is a number which can vary typically from about 1 to about 4, preferably from about 1 to about 3, and most preferably from about 1 to about 2 (e.g., 1); and n" is a number which typically can vary on any individual carbamate from 0 to 5 or higher. Commercially, the resulting carbamates will typically comprise a mixture of carbamates represented by structural formula IV wherein the average value of n" in said mixture typically will vary from about 1 to about 3.5, preferably from about 2.2 to about 3.0, and most preferably from about 2.5 to about 2.8. It is also contemplated that R$_3$ can be halogen substituted.

(5) Conversion of Polycarbamate to Polyisocyanate

The carbamic acid ester groups on the aforedescribed condensed carbamates are optionally converted to isocyanates and alcohols by any technique capable of achieving this effect. This can be achieved by thermolysis wherein the carbamates are heated (preferably in solution) to a temperature effective to split off an alcohol group from the carbamic acid ester group forming the corresponding free isocyanate group and alcohol. This can be achieved in the presence of a catalyst as described in U.S. Pat. No. 3,919,279, or in the absence of a catalyst in accordance with U.S. Pat. No. 3,962,302, the disclosures of said patents being herein incorporated by reference.

Effective thermolysis temperatures can vary typically from about 175 to about 350, preferably from about 200 to about 300, and most preferably from about 230° to about 285° C. Typical catalysts include molybdenum oxide, vanadium pentoxide, manganese oxide, iron oxide, chromic oxide, or organic complexes such as acetylacetonates of vanadium, manganese, cobalt and copper. Inorganic and organic salts such as iron chloride, iron bromide, vanadium naphthanate, nickel acetate, and copper stearates also can be used.

Suitable solvents include ortho-terphenyl, tetrahydronaphthalene, alkylbenzene, n-hexadecane, n-octadecane and di-2-ethylhexylphthalate.

A preferred method for the thermolysis of aromatic carbamates is disclosed in commonly assigned U.S. patent application Ser. No. 343,584 filed Jan. 28, 1982; for "Production of Isocyanates from Esters of Aromatic Carbamic Acids" by R. Spohn, the disclosure of which is herein incorporated by reference. This application describes the use of at least one catalyst to facilitate the thermolysis reaction comprising at least one metal, preferably utilized in the form of at least one metal containing polar compound, preferably polar organo compound, said metal being selected from the group consisting of Ti, Sn, Sb, Zr and mixtures thereof. Tin is the most preferred metal. For homogeneous reactions these metal containing compounds are preferably selected in conjunction with a suitable inert organic solvent such that metal moiety (with which the catalytic activity is associated) is soluble therein. The thermolysis in this embodiment is conducted at atmospheric or super atmospheric pressure.

The isocyanates can be separated from the alcohol by any conventional means such as by sweeping the alcohol and/or isocyanate out of the reaction mixture with an inert gas or suitable solvent. Separation is then carried out by fractionation or partial condensation.

The resulting isocyanate can be represented by the structural formula:

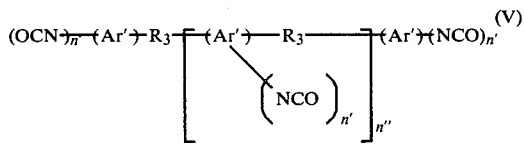

(V)

wherein Ar', R₃, n', and n" are as described in structural formula IV. The isocyanate forming step is optional, since for certain applications masked isocyanates, i.e., carbamates of structural formula IV which act in situ at elevated temperatures as isocyanates by splitting off alcohol, can be employed directly. However, for other applications, masked isocyanates cannot be used directly. It is in these applications where the final isocyanate forming step is employed.

Advantages of the Process

Benzene is the common starting material for both the referenced phosgene and carbonylation processes.

Since benzene separated from naphtha reformate is not sufficient for the benzene demand in the chemical industry, it has been produced via dealkylation of toluene and transalkylation of toluene to benzene and xylene isomers. Thus the advantages of toluene in place of benzene are use of cheaper, more abundant raw material and energy saving. Use of NH₃ as a reactant results in the saving of material and energy and elimination of a corrosion problem. Since the new process does not use toxic compounds such as phosgene, carbon monoxide, benzene and catalyst selenium compounds, it offers an environmentally less hazardous procedure for the manufacture of polyisocyanates. Elimination of the anhydrous reaction conditions means a further savings in energy and cost effectiveness.

The invention will be further understood by reference to the following examples which include preferred embodiments of the invention.

The following examples are given as specific illustrations of the claimed invention. It should be understood, however, that the invention is not limited to the specific details set forth in the examples. All parts and percentages in the examples as well as in the remainder of the specification are by weight unless otherwise specified.

AMMOXIDATION OF TOLUENE TO BENZONITRILE

Example 1

Vapor Phase 5 cc of a catalyst, chromia (5%)-vanadia (5%) on alumina catalyst (0.5 m²/g), is loaded in a microreactor (¼" ID). A mixture of toluene, ammonia, air and steam is passed over the catalyst at 490° C. The feed rate is 0.06 weight-hour-space-velocity (WHSV) based on toluene with a 14 mole ratio of O₂ to toluene, a 24 mole ratio of water to toluene, and a 4 mole ratio of NH₃ to toluene is feed. The product analysis shows the following results: the conversion of toluene is higher than 90%; and mole selectivities to benzonitrile for toluene and ammonia are higher than 99% and 95%, respectively.

Example 2

Liquid Phase 65.58 gms of benzonitrile was placed in a 100 ml flask. 1.15 gms of manganese diacetate (MnAc₂.4H₂O) and 0.46 gms of NH₄Br was added to the flask. The flask was equipped with a condenser to collect water, toluene and benzonitrile which could be vaporized out, and a mechanical stirring device. Approximately 120 cc/min. N₂ gas flow was passed through the flask and then the flask was heated to 125° C. to dissolve the solids. After the addition of a small amount of toluene to the flask and then switching N₂ gas flow to 100 cc/min. air flow, the heating was continued to 168° C. After toluene oxidation at 168°-174° C. for 1 hr., the air flow was bubbled through an aqueous concentrated NH₄OH solution in an ice bath and then introduced into the flask. The toluene ammoxidation reaction was continued at 174°-178° C. When the toluene in the flask was depleted to low concentration (~1%), toluene was added from time to time, maintaining the reaction temperature in a range of 174°-178° C. After 7 hrs. 54 min. of the ammoxidation reaction conditions, the total product weight in the flask was 72.89 gms (excluding weight of catalyst). Therefor, about 7.31 gms product was produced by toluene ammoxidation. The Gas Chromatographic (G.C.) analysis of the product showed that about 2.5% of the product was benzamide. Benzamide was the only detectable product other than benzonitrile.

CONVERSION OF BENZONITRILE TO BENZAMIDE

Example 3

Benzonitrile (44.85 g) and 0.76 g MnO₂ powder were placed in a flask and the mixture was heated to 120° C. with mechanical stirring under N₂ atmosphere. Water was slowly added while maintaining the hydrolysis temperature at 115°-130° C. After 7 hrs., the product was analyzed. The product contained 26.98 wt. % benzamide. Benzamide was the only reaction product.

CONVERSION OF BENZAMIDE TO CARBAMATE

Example 4

A 250 ml-4-necked micro flask was equipped with an electrically driven single blade stirrer, thermometer, feed inlet and bath. 75 mmoles of benzamide was weighed into the flask and 45 ml of methanol (sufficient to give a 20 w/v % solution of amide in solvent) was added. Sodium methoxide (80 mmoles) was added cautiously with cooling and chlorobenzene (12 mmoles) was introduced as the G.C. internal standard. t-Butyl hypochlorite (82 mmoles) was pumped into the reactor over a one hour period. The temperature was maintained at 20° C. and light was excluded. Stirring was continued for one hour after which the temperature was raised to 50° C. and maintained there for one hour. The reactor on cooling contained a solid and a liquid phase. The solid was filtered off and washed with methanol. The solid filter cake was dried, weighed, and analyzed for sodium chloride after dissolution with water. The aqueous solution was examined for by-product organic material and these were separated to give by-product yield. G.C. analysis of the filtrate was obtained and the results are tabulated in Table 1 which also sets forth the data for the following Examples 4-8.

The insoluble by-product was identified as 1-benzoyl-3-phenyl urea by melting point measurement and IR spectra.

Example 5

This example is the same as the Example 4 except that the reaction temperature was raised to 45° C. and maintained at this temperature for a one hour period.

This example shows the reaction temperature effect. As shown in Table 1, the selectivity to carbamate and phenyl isocyanate greatly improved compared with Example 4, whose reaction temperature was 20° C. This selectivity improvement was achieved by preventing the formation of 1-benzoyl-3-phenyl urea which normally would form by additive reaction of benzamide to isocyanate during the course of the reactions at the lower reaction temperatures.

Example 6

The equipment, conditions, and reactants were the same as that described in Example 4 except that 50.6 wt. % aqueous sodium hydroxide was used as the base in place of the methanolic sodium alkoxide solution and the post reaction time was reduced to thirty minutes.

The purpose of this example was to determine the water effect by carrying out the reaction in the presence of water. As shown in Table 1, the selectivity was excellent, although the conversion of benzamide was lower than those of Examples 3 and 4. There were no by-products such as aniline or diphenyl urea ($C_6H_5NHCONHC_6H_5$) which could be expected from the presence of water.

Example 7

This example is the same in all respects as that described in Example 6 except that the reaction temperature was set at 60° C., and the methanol solvent concentration was increased so as to give a benzamide concentration of 10 w/v %. The post reaction time was thirty minutes at 60° C.

By carrying out the reaction with diluent benzamide solution at a higher temperature (60° C.), lower conversion of benzamide in the presence of water as shown in Example 6, was improved as shown in Table 1. The selectivity was excellent.

Example 8

Except for a modification in the manner of base addition and post reaction time, the conditions for this example were the same as those described in Example 7. The amount of methanol ultimately added to the reactor was calculated to give a final concentration of 10 w/v % benzamide in methanol. One half the methanol used was used to prepare the benzamide solution and the other half was used to dilute the aqueous sodium hydroxide solution before it was pumped into the reactor. An amount of base solution equivalent to 20% of that required was added to the reactor prior to the simultaneous addition of the t-butyl hypochlorite and the remaining base. There was no post reaction time in this example. As shown in Table 1, both conversion and selectivity were excellent.

CONDENSATION WITH FORMALDEHYDE

Example 9

150 g methyl N-phenyl carbamate and 400 cc water is heated to 93° C. with mechanical stirring. 53.7 g of 37% formaldehyde solution is slowly added to the above mixture, and then 100 cc of concentrated HCl is slowly added while maintaining the temperature at 90°–93° C. The temperature of the mixture is maintained at 93° C. for 24 hours with vigorous mechanical stirring. The upper layer is removed by decanting. The remaining product is washed three times with 200 cc of hot water. The washed product is placed in a fractional distillation apparatus. Water, trace formaldehyde, and unconverted methyl N-phenyl carbamate are removed by vacuum fractional distillation. The condensation product of carbamate and formaldehyde is concentrated in the flask and recovered.

THERMAL DECOMPOSITION OF POLY(CARBAMATE)

Example 10

11.0 wt. % 4,4'-methylene bis(N-phenyl methyl carbamate) (MDC) solution in benzene is prepared. 1" ID glass tube is filled with 40 cc ⅛" glass balls and heated to 250° C. in a vertical tube furnace with 100 cc/min. $N_2$ flow. The MDC solution is thermally cracked to MDI and methanol by passing the MDC solution downflow through the glass ball packed tube. The MDC solution is fed to the reactor at the rate of 45 g/hr. The alcohol and solvent benzene from the MDI and MDC are separated by feeding the hot reactor effluent directly to a flash separation column. The mixture of MDI and MDC was removed from the bottom of the separation column. The product analysis will show 35% conversion of MDC to MDI.

This invention also has applicability to the preparation of non-condensed isocyanates, such as 2,4-toluene diisocyanate and 1,4-xylene diisocyanate from methylated aromatics, such as 1,2,4-trimethylbenzene and p-xylene respectively, when the condensation step of the multireaction step process of the invention is eliminated. For example, a preferred process for making an aromatic diisocyanate such as 2,4-toluene diisocyanate and 1,4-phenylene diisocyanate in accordance with the present invention comprises.

(a) reacting an alkylated (e.g. 1 to 5 carbons), preferably a methylated compound of the formula $C_6H_{6-s}(R_1)_s$ wherein s is 1 to 5, and $R_1$ is as described in connection with structural formula I, and is preferably methyl; with ammonia and oxygen under ammoxidizing conditions, thereby forming an aromatic dinitrile of the formula $C_6H_{4-t}(R_1)(CN)_2$ wherein t is 0 to 3 (e.g., 2,4-dicyanotoluene is formed from 1,2,4-trimethyl benzene and 1,4 dicyanobenzene is formed from p-xylene);

(b) hydrolyzing said aromatic dinitrile by heating it at a temperature of from about 50° to 200° C. in the presence of water, thereby forming an aromatic diamide of the formula $C_6H_{4-t}(R_1)_2(CONH_2)_2$;

(c) admixing an alcoholic solution of said diamide with a N-halogenating agent and alkali base at a temperature of at least 40° C. and in the presence of at least 2 wt. % water based on the weight of said amide, thereby producing an aqueous-alcoholic solution of N-aryl alkyl dicarbamate of the formula:

$$C_6H_{4-t}(R_1)_t(NCO_2R_2)_2$$

wherein $R_2$ is as described in connection with structural formula III, and (d) thermally decomposing said dicarbamate and separately recovering the alcohol and said aromatic diisocyanate.

The non-condensed process has utility also in production of aromatic isocyanates such as phenyl isocyanate from toluene or naphthyl isocyanate from methyl naphthalene. Further, since the inventive process utilizes a monocarbamate prior to cracking to recover the monoisocyanate, it is obvious to use the process for the production of aromatic monocarbamates by elimination of the cracking step.

The invention in its broader aspect is not limited to the specific details shown and described and departures may be made from such details without departing from the principles of the invention and without sacrificing its chief advantages.

sufficient to form at least one carbamate compound represented by the structural formula:

$$(Ar')-(NHCO_2R_2)_n \qquad (III)$$

wherein $R_2$ represents a hydrocarbyl group independently selected from alkyl having from about 1 to about 10 carbons, aryl having from about 6 to about 14 carbons, alkaryl and aralkyl wherein the alkyl and aryl groups thereof are as described im-

TABLE 1

| Example No. | 4 | 5 | 6 | 7 | 8 |
|---|---|---|---|---|---|
| Wt. % of B.A. in solution | 20 | 20 | 20 | 10 | 10 |
| Base | CH$_3$ONa | CH$_3$ONa | 50% aq. NaOH Sol. | 50% aq. NaOH Sol. | 50% aq. NaOH Sol. |
| Mode Base Addition | in soln. with B.A. | in soln. with B.A. | in soln. with B.A. | in soln. with B.A. | S.A. |
| Reaction Time (min.) | 60 | 60 | 60 | 60 | 60 |
| Reaction Temp. (°C.) | 20 | 45 | 45 | 60 | 60 |
| Product Analysis (m mole) | | | | | |
| B.A. | 5.40 | 7.48 | 11.13 | 7.20 | 0.38 |
| Phenylisocyanate | 1.96 | 0.72 | 1.00 | 0.70 | 0.43 |
| Methyl Benzoate | 0.64 | 0.49 | 0.50 | 0.30 | 0.23 |
| By-Product (Insoluble) | 7.60 | 0 | 0 | 0 | 0 |
| Carbamate | 59.40 | 58.3 | 52.5 | 59.90 | 66.5 |
| B.A. Conversion (%) | 93.5 | 89.0 | 82.9 | 89.4 | 99.4 |
| Selectivity to Carbamate and phenylisocyanate (mole %) | 79.5 | 97.5 | 99.1 | 99.5 | 99.7 |
| Mass Balance Benzamide (%) | 109.7 | 90.3 | 86.5 | 90.4 | 89.7 |

B.A. = Benzamide
S.A. = 80% base was added to the benzamide solution simultaneously with t-BuOCl and 20% base was mixed with the benzamide solution prior to that.

What is claimed is:

1. A process for making an aromatic polycarbamate which comprises:

(a) reacting at least one compound represented by the structural formula:

$$(Ar)-(R_1)_n \qquad (I)$$

wherein Ar is a halogen substituted or unsubstituted aromatic hydrocarbyl group, $R_1$ is an alkyl group having from about 1 to about 10 carbons, and n is a number which can vary from 1 to about 5; with ammonia and oxygen under conditions and in a manner sufficient to form at least one aromatic nitrile containing compound represented by the structural formula:

$$(Ar')-(CN)_n \qquad (Ia)$$

wherein Ar' is a substituted or unsubstituted aromatic hydrocarbyl group having from about 6 to about 14 carbons exclusive of substituents; said substituents on Ar' being selected from the group consisting of halogen, alkyl having from about 1 to about 10 carbons, and mixtures thereof; and n is as described in connection with structural formula I;

(b) hydrolyzing said aromatic nitrile containing compound in a manner and under conditions sufficient to form at least one amide represented by the structural formula:

$$(Ar')-(CONH_2)_n \qquad (II)$$

wherein Ar' and n are as described in connection with structural formula Ia above;

(c) converting at least one of said amide groups present on the compound of structural formula II to a carbamate group in a manner and under conditions mediately above, and cycloalkyl having from about 4 to about 10 carbons; and Ar' and n are as described in connection with structural formula Ia; and (d) condensing the carbamate with a carbonyl containing compound in a manner and under conditions sufficient to form at least one aromatic polycarbamate represented by the structural formula:

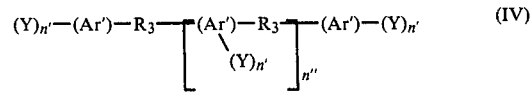

wherein: Y represents the group —NHCO$_2$R$_2$, R$_2$ being as described above; R$_3$ is a hydrocarbyl group independently selected from alkylene having from about 1 to about 10 carbons, arylene having from 6 to about 14 carbons, aralkylene and alkarylene wherein the alkyl and aryl portions thereof are as described above, and cycloalkylene having from about 4 to about 10 carbons; n' is a number which can vary from about 1 to about 4; n'' is a number which can vary from about 0 to about 5; and Ar' is as described in connection with structural formula III.

2. The process of claim 1 wherein the aromatic polycarbamate of step (d) is subjected to reaction conditions in a manner sufficient to form an aromatic polyisocyanate represented by the structural formula:

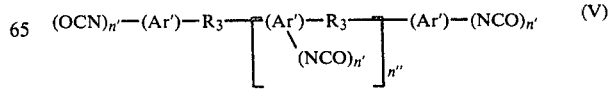

wherein Ar', $R_3$, n', and n" are described in structural formula IV of claim 1.

3. The process of any one of claims 1 or 2 wherein Ar is phenyl, $R_1$ is methyl or ethyl, the aromatic hydrocarbyl group constituting Ar', exclusive of substituents, contains 6 carbons, $R_3$ is methylene, and n and n' are numbers which can vary from 1 to 2.

4. The process of claim 1 wherein the aromatic nitrile is hydrolyzed to form said amide by heating it at a temperature of from 50° to 200° C. in the presence of water; the amide is converted to the carbamate by admixing an alcoholic solution of said amide with a N-halogenating agent and alkali base at a temperature of at least 40° C. and in the presence of at least 2 weight percent water based on the weight of said amide; and the carbamate is condensed with formaldehyde at a temperature of from about 50° to about 200° C.

5. The process of claim 2 wherein the carbamate is heated in the presence of a solvent to a temperature of from about 175° to about 300° C.

6. The process of claim 1 wherein condensation step d is omitted and n is 2 thereby forming a dicarbamate.

7. The process of claim 6 wherein the resulting dicarbamate is converted to a diisocyanate.

8. The process of any one of claims 6 or 7 wherein Ar and Ar' contain 6 carbons, $R_2$ is methyl or ethyl, and $R_1$ is methyl.

* * * * *